United States Patent [19]
Flower et al.

[11] Patent Number: 6,009,344
[45] Date of Patent: Dec. 28, 1999

[54] IONTOPHORETIC DRUG DELIVERY SYSTEM

[75] Inventors: Ronald J. Flower, Lawrenceville, Ga.; Kenneth E. Garde, New Windsor, N.Y.

[73] Assignee: Becton, Dickinson and Company, Franklin Lakes, N.J.

[21] Appl. No.: 08/900,889

[22] Filed: Jul. 25, 1997

[51] Int. Cl.[6] .................................................. A61N 1/30
[52] U.S. Cl. .............................................. 604/20; 604/75
[58] Field of Search .............................. 604/20; 607/152, 607/153, 75

[56] References Cited

U.S. PATENT DOCUMENTS

| | | | |
|---|---|---|---|
| 4,149,533 | 4/1979 | Ishikawa et al. | 604/20 |
| 4,725,263 | 2/1988 | McNichols et al. | 604/20 |
| 5,314,502 | 5/1994 | McNichols et al. | 604/20 |
| 5,387,189 | 2/1995 | Gory et al. | 604/20 |
| 5,431,625 | 7/1995 | Fabian et al. | 604/20 |
| 5,591,123 | 1/1997 | Sibalis et al. | 604/20 |
| 5,695,459 | 12/1997 | Meguro | 604/20 |

*Primary Examiner*—Wynn Wood Coggins
*Assistant Examiner*—Sharon Finkel
*Attorney, Agent, or Firm*—Authur D. Dawson

[57] ABSTRACT

An iontophoretic drug delivery system of the present invention includes a controller interconnectable with a drug-filled patch. The controller includes electronic circuitry which monitors and controls the supply of electrical current to the drug-filled patch during delivery of at least one drug, and the electronic circuitry includes a circuit for causing a voltage step in a battery of a plurality of serially-connected cells. Specifically, the circuit causes one or more of the cells to discharge through a resistor at a higher rate than the other cells, thus producing a voltage step when the faster discharging cell dies before the other cells. A reverse-biased diode is connected in parallel to the faster discharging cell to cause the current to bypass the faster discharging cell after it has died, thus preventing it from reverse charging. This circuitry may be controlled to adjust the higher rate of discharge, and thus the time of occurrence of the voltage step.

5 Claims, 11 Drawing Sheets

IONTOPHORETIC DRUG DELIVERY SYSTEM

FIELD OF THE INVENTION

The present invention generally relates to iontophoretic drug delivery systems, and more specifically relates to an iontophoretic drug delivery system for delivering drugs or medicines to patients transdermally, i.e., through the skin, including electronic circuitry for causing a voltage step in a battery comprising a plurality of serially-connected cells. In a preferred embodiment of the present invention, this voltage-step causing circuitry is employed in a controller of the iontophoretic drug delivery system.

BACKGROUND OF THE INVENTION

Transdermal drug delivery systems have, in recent years, become an increasingly important means of administering drugs and like therapeutic agents.

Presently, there are two types of transdermal drug delivery systems, i.e., "Passive" and "Active." Passive systems deliver drug through the skin of the user unaided, an example of which would involve the application of a topical anesthetic to provide localized relief, as disclosed in U.S. Pat. No. 3,814,095 (Lubens). Active systems on the other hand deliver drug through the skin of the user using, for example, iontophoresis, which according to Stedman's Medical Dictionary, is defined as "the introduction into the tissues, by means of an electric current, of the ions of a chosen medicament." Such systems offer advantages clearly not achievable by any other methods of administration, such as avoiding introduction of the drug through the gastro-intestinal tract or punctures in the skin to name a few.

Conventional iontophoretic devices, such as those described in U.S. Pat. Nos. 5,498,235 (Flower), 5,540,669 (Sage, Jr. et al.), and 5,645,526 (Flower), the disclosures of which are hereby incorporated by reference, for delivering a drug or medicine transdermally through iontophoresis, basically consist of two electrodes, which are in contact with a portion of a patient's body. A first electrode, generally called the active electrode, delivers the ionic substance or drug into the body by iontophoresis. The second electrode, generally called the counter electrode, closes an electrical circuit that includes the first electrode and the patient's body. Generally, the circuit includes a source of electrical energy, such as a battery. The ionic substance to be driven into the body may be either positively charged or negatively charged. In the case of a positively charged ionic substance, the anode of the iontophoretic device becomes the active electrode and the cathode serves as the counter electrode to complete the circuit. Alternatively, if the ionic substance to be iontophoretically delivered is negatively charged, the cathode will be the active electrode and the anode will be the counter electrode.

In practice, this process is typically achieved by placing the ionic drug either in solution or in gel form on a carrier and placing the drug-containing carrier, for example, in the form of a drug-filled adhesive patch, into contact with the skin, with the patch being electrically and mechanically connected to a controller. The controller includes a power source, such as a battery, as well as electrical circuitry required for generating and regulating current applied to the electrodes contained in the patch.

The pair of electrodes is placed in contact with the skin and with the carrier. Direct current is applied between the two electrodes. Under the influence of the electric field present, the drug molecules migrate through the skin. As current flows between the two electrodes placed at spaced apart locations on the skin, the current path carries the drug with it.

In order to deliver the drug to the patient, the adhesive patch may be applied to the desired portion of the patient's body and the controller attached to the patch. Oftentimes the controller is as large as, or larger than, the patch. It also should be somehow secured in place on the patient so that the patient may remain mobile and carry both the patch and controller with him as he moves about.

Delivery of a drug to the patient iontophoretically may be accomplished either at a constant rate over a long period of time, or periodically at various intervals and in some situations, upon demand. As can be seen, it may be necessary for the drug-containing carrier to be maintained in contact with the patient's skin over a long period of time, either for continuous drug delivery, or to permit frequent interval delivery over a period of time.

As previously noted, it may be necessary to use an iontophoretic drug delivery system over an extended period of time i.e., longer than 24 hours to delivery the necessary dosage of drug. As the length of delivery time increases, there is a need to develop small, unobtrusive iontophoretic delivery devices which can be easily worn on the skin under clothing. Also, it is envisioned that the controller may contain sophisticated electronics along with the battery to control and monitor the delivery of drug to the patient.

Figure 1A:
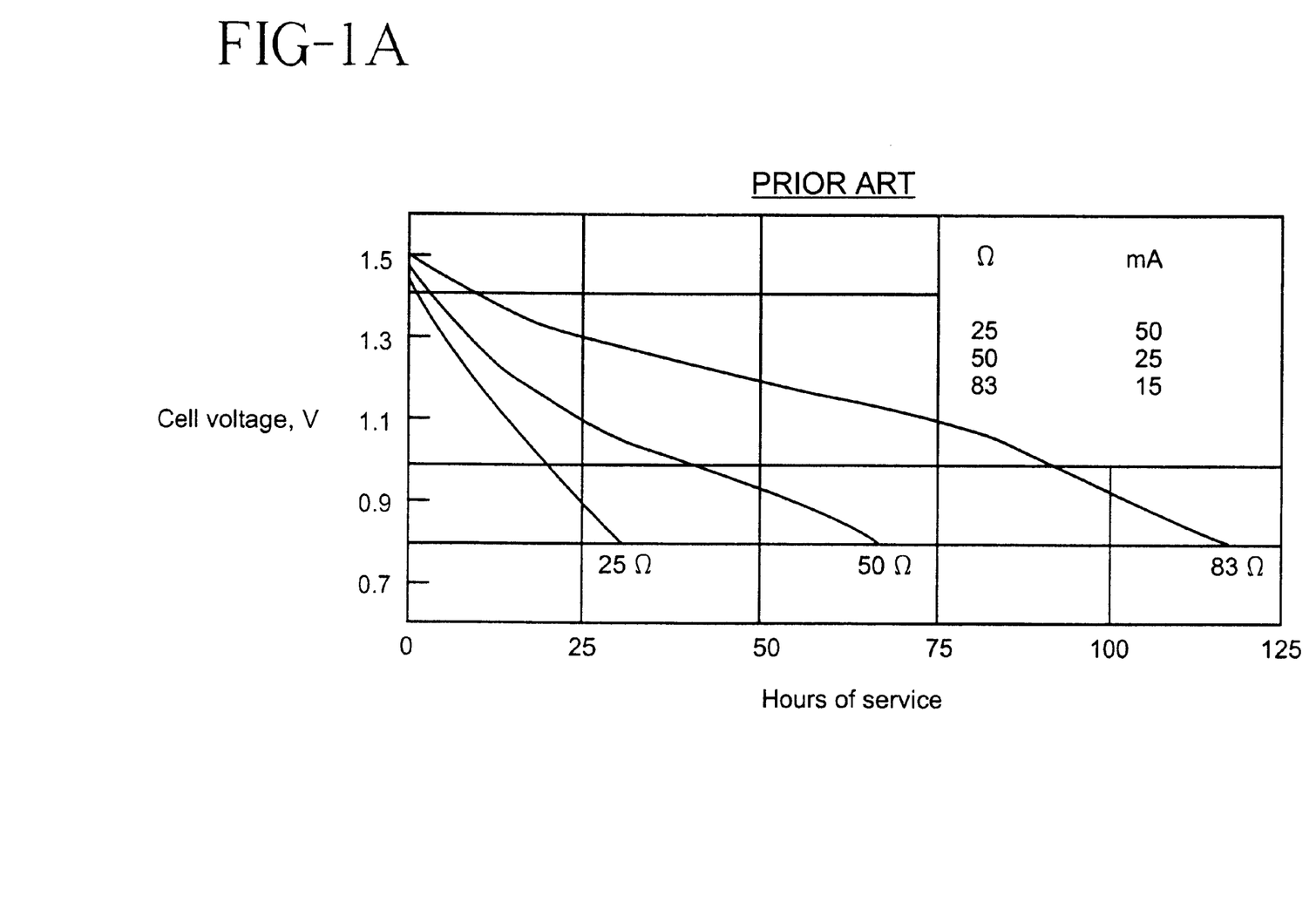
FIG. 1A depicts a battery discharge curve for a conventional alkaline battery.

The output voltage of the battery is often used as an indicator of the energy remaining in the battery. That output voltage may be monitored by a voltage monitoring circuit, either internally connected to the device to which the battery supplies energy or externally connected to that device. The output voltage of some types of batteries, such as alkaline manganese dioxide $Zn/MnO_2$ batteries (hereinafter referred to as "alkaline" batteries) gradually decreases, as shown in FIG. 1A (corresponding to Fig. 7.5 of the Handbook of Batteries, edited by David Linden, 1984). When the monitoring circuit has detected that the output voltage has decreased below a predetermined voltage level, there might be enough energy left in the battery for the device to complete a critical ongoing task, such as drug delivery in an iontophoretic drug delivery system, as described below, or to perform an essential power-down function, such as memory backup in a battery-powered computer. These types of batteries, however, may not be preferred for certain applications which require batteries with high energy and high current capacity.

Figure 1B:
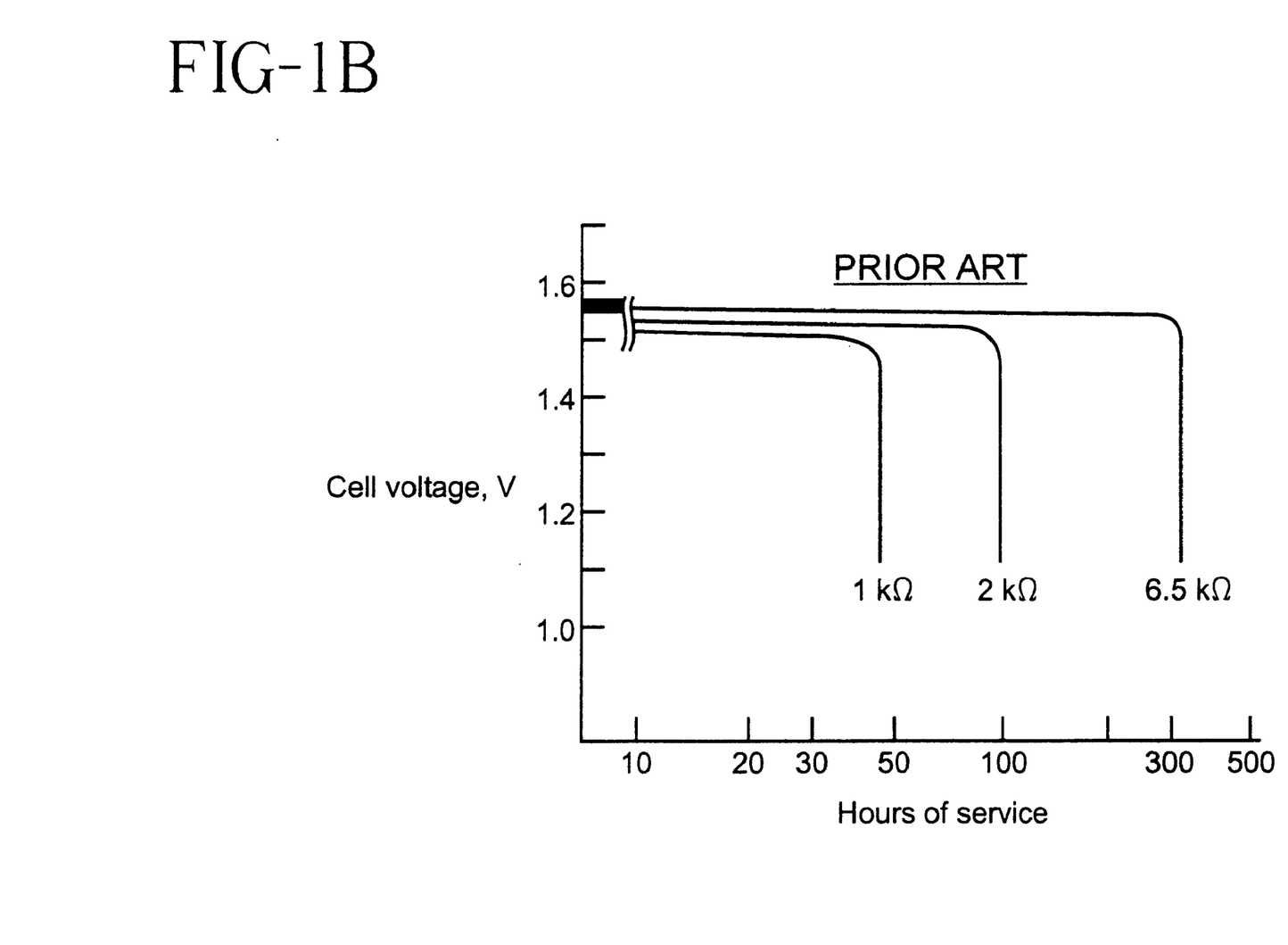
FIG. 1B depicts a battery discharge curve for a conventional silver oxide battery.

Other conventional batteries, such as zinc/silver oxide batteries ($Zn/Ag_2O$, hereinafter referred to a "silver oxide batteries"), are characterized by a substantially flat output voltage over time, until the cells of the battery die, at which time the output voltage sharply decreases, as shown by FIG. 1B (corresponding to Fig. 9.4 of the Handbook of Batteries). Despite this discharge characteristic, silver oxide batteries are preferred for certain electrical applications because they are small, thin and light, and deliver a high amount of current for a long period of time. When the voltage monitoring circuit has detected that the output voltage of the battery has begun to decrease sharply, there may not be enough energy left in the battery, however, for the device to complete a critical ongoing task or to perform an essential power-down function. Therefore, there is a need for a high quality, high-current delivering battery, such as the conventional silver oxide battery, which also has enough remaining energy, after the voltage monitoring circuit has detected the sharp decrease in the output voltage, to allow the device to complete its task or to power-down.

Figure 1C:
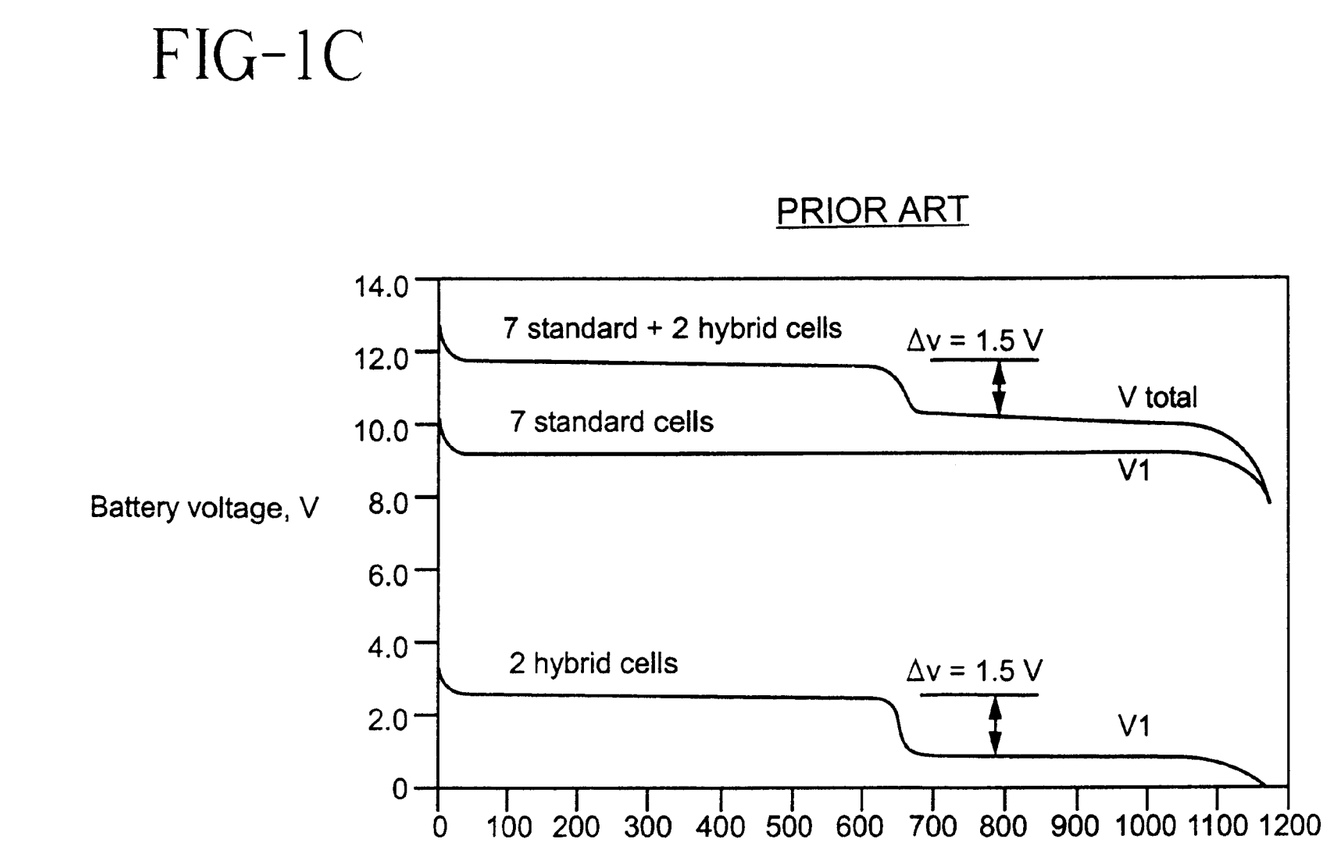
FIG. 1C depicts a battery discharge curve for a conventional stepped-discharge battery.

Section 8.5.7 of the Handbook of Batteries describes a "stepped-voltage" battery which produces a well-defined step in the output voltage prior to its complete discharge, as shown in FIG. 1C (corresponding to Fig. 8.25 of the Handbook of Batteries). This voltage step occurs well before the end of battery life so that, after the voltage monitoring circuit has detected the voltage step, enough energy remains in the battery to allow the device to complete a final task or to power-down. The stepped-voltage battery is made by using materials in the cathode or the anode of the battery which discharge at a different potential from the base electrode.

In particular, FIG. 1C shows a nine-cell battery having a stepped battery voltage discharge curve $V_{total}$, which is produced by serially connecting seven zinc/mercuric oxide cells that together are characterized by the substantially flat voltage discharge curve $V_2$, and two hybrid cells that together are characterized by the stepped voltage discharge curve $V_1$. The hybrid cells have cathodes in which part of the mercuric oxide has been replaced by cadmium oxide in a sufficient quantity to leave each hybrid cell with the same balanced capacity. When all of the mercuric oxide has been reduced in the hybrid cells, that is, the hybrid cells have discharged, their combined voltage falls by 1.5 Volts (750 millivolt per hybrid cell), as shown in curve $V_1$. This causes the combined voltage $V_{total}$ to decrease by 1.5 Volts. This sudden, large drop in the output voltage can be easily detected by the voltage monitoring circuit, and thus can serve to trigger an alarm indicating the need for battery replacement, or to warn the device that any ongoing task should be a final task or that the device should begin powering down. The size of the voltage step can be adjusted, for example, by increasing or decreasing the number of hybrid cells in the battery. Further, during manufacture of the stepped-voltage battery, the voltage step can be arranged to occur at varying points during the life of the battery. For example, in the nine-cell battery of FIG. 1C, the voltage step was arranged to occur at about 60% (650 hours) of the overall life (1100 hours).

The above-described stepped-voltage batteries are, however, limited in their use, especially as a substitute for silver oxide batteries and the like. First, all the cells of the stepped-voltage battery are arranged in a relatively large, wide and heavy package, making its use impractical for small or thin electronic devices. Second, relative to silver oxide batteries, stepped-voltage batteries are expensive and have a lower current capacity. Third, to meet all of the different energy requirements of various devices, a device manufacturer would need to order and stock, unfortunately, many different types of stepped-voltage batteries. Finally, although the time at which the voltage step of the stepped-voltage battery occurs can be set as described above, that setting is set during manufacturing and cannot be adjusted thereafter. It would be more desirable to be able to use a battery with which the time of the voltage step can be adjusted while the device is being operated. Such time adjustment can be based on the operating conditions of the device using, for example, computer control.

Thus, there has been a need for an iontophoretic drug delivery system, particularly a controller which would eliminate the problems and limitations associated with the prior devices discussed above, most significant of the problems being the need for a time-adjustable, stepped-voltage output when use of a more practical and desirable conventional battery, such as a silver oxide battery, is required by the device.

SUMMARY OF THE INVENTION

In contrast to the prior devices discussed above, it has been found that a iontophoretic drug delivery system including a controller having electronic circuitry advantageously causes a voltage step in a battery of a plurality of serially-connected cells so that the voltage step may be detected and acted upon is particularly suited for use in connection with the iontophoretic delivery of the drug, medicament or the like. In addition, the circuit causes one (or more) of the cells to discharge through a resistor at a higher rate than the other cells, thus producing a voltage step when the faster discharging cell dies before the other cells. A reverse-biased diode is connected in parallel to the faster discharging cell to cause the current to bypass the faster discharging cell after it has discharged, thus preventing that cell from reverse charging. This circuit may be controlled to adjust the time of occurrence of the voltage step.

In another aspect of the present invention, another diode is connected in series with the resistor to prevent the other cells from discharging through the resistor if the battery is connected to a push-pull switch in the device.

In yet another aspect of the present invention, multiple resistor and diode circuits are added to provide multiple voltage steps.

BRIEF DESCRIPTION OF THE DRAWINGS

The various features, objects, benefits, and advantages of the present invention will become more apparent upon reading the following detailed description of the preferred embodiment along with the appended claims in conjunction with the drawings, wherein like reference numerals identify corresponding components, and:

DETAILED DESCRIPTION OF THE PREFERRED EMBODIMENTS

The iontophoretic drug delivery system 70 of the present invention is illustrated in FIGS. 2–7, with the system including a controller generally designated 80 and a patch generally designated 60.

Figure 2A:
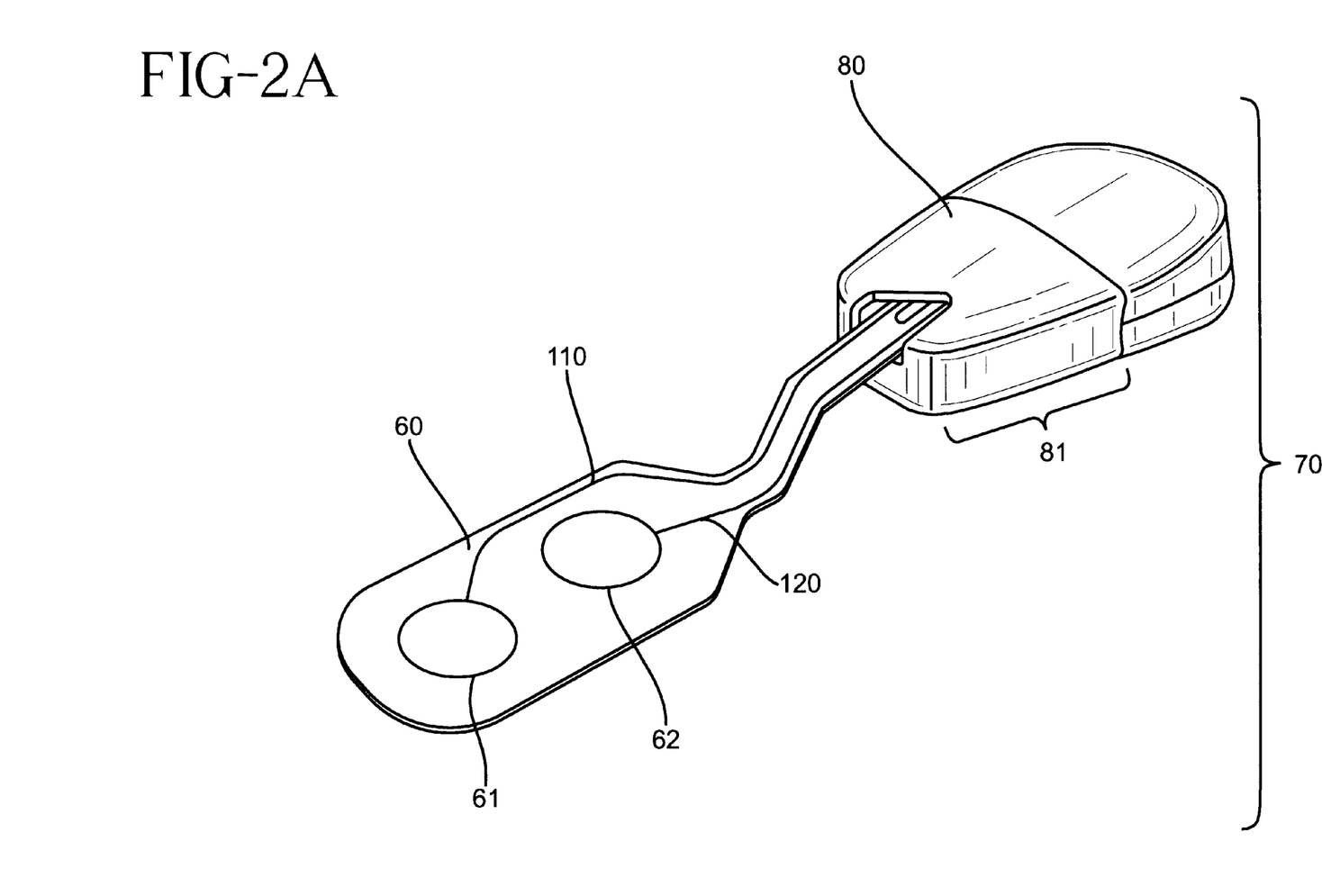
FIGS. 2A and 2B depict the iontophoretic drug delivery system of the present invention.
Figure 2B:
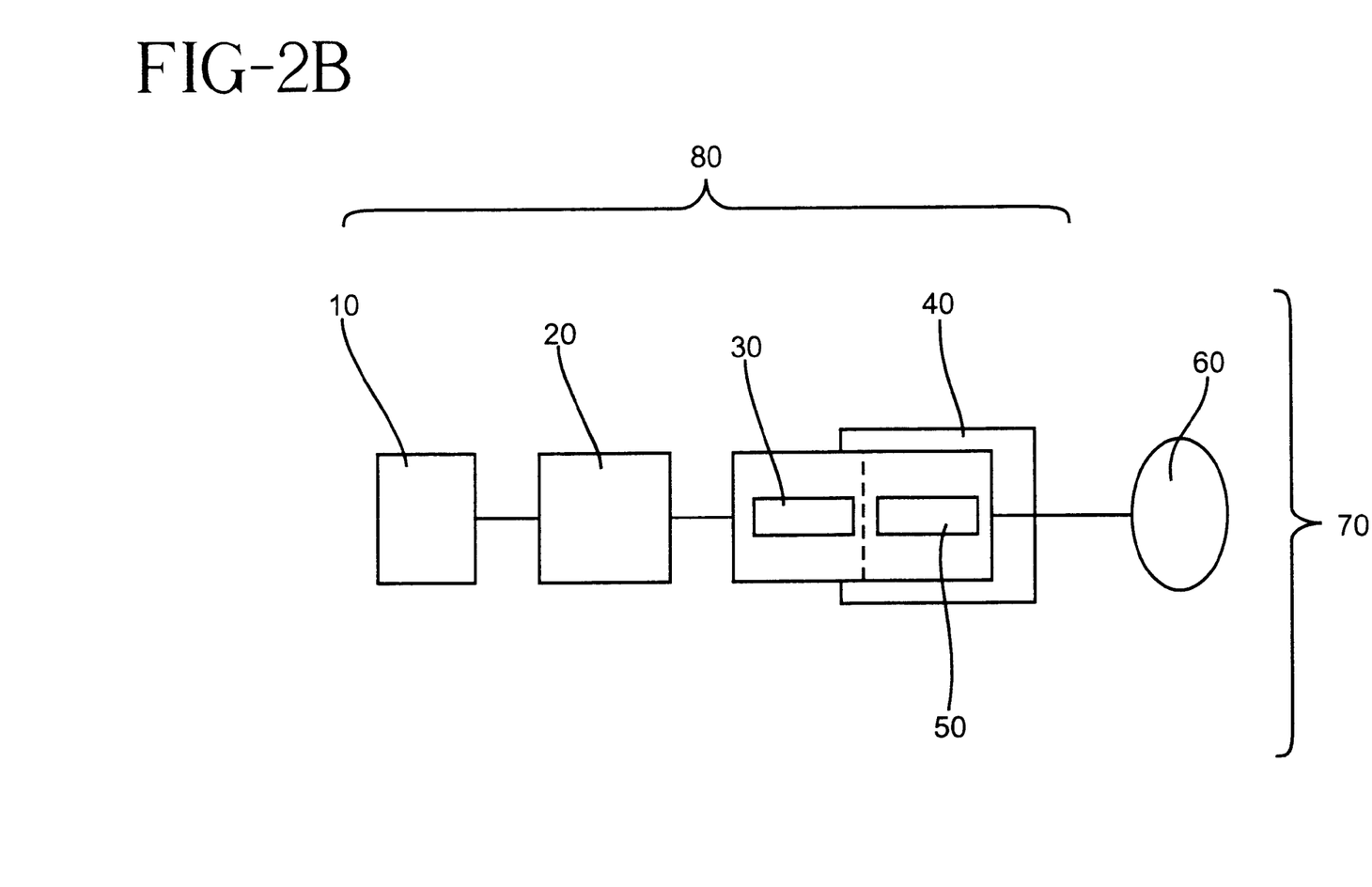

Referring to FIGS. 2A and 2B, the controller 80, including the battery, is respectively connected to an anode 61 and cathode 62 in the patch 60 via the electrical interconnectors 110 and 120. The controller 80 includes an outer casing 81 which houses the power source and current generation and regulation circuitry required for driving current into the patch 60. The casing of the controller 80 may be made of a plastic, metal or other suitable material for encasing and protecting the current regulating circuitry. The patch electrodes 61 and 62 electrically connect to the current controller 80 via electrical connectors 110 and 120. It should be appreciated by one skilled in the art that the system of the present invention may include a separate controller and interconnectable patch, or the patch and controlled may integrated into a single integral system.

The anode 61 is arranged in the active reservoir containing or filled with a positively-charged drug, while the cathode 62 is arranged in the return reservoir containing the electrolytic (or saline) solution. If the drug is negatively-charged, the anode and cathode arrangement in the reservoirs is reversed, so that when current is applied to the electrodes, drug ions will be repelled from the reservoir of similar polarity. When the patch 60 is placed on the skin of a user and the controller applies current to the patch 60, the charged drug is forced into the skin and blood of the patient. Ions charged oppositely of the drug ions are returned to the return reservoir as the body completes the iontophoretic circuit. For example, if the drug is negatively-charged, a AgCl cathode will repel them through the skin and into the blood vessel, while positively-charged sodium ions are attracted to the cathode. At the same time, negatively-charge chlorine ions will flow from the skin into the return reservoir containing saline toward the anode.

The controller 80 usually includes a microprocessor or state machine to implement the numerous control functions. For example, a microprocessor executes software programs which, inter alia, command the current generation and regulation circuitry to provide the required amount of current over a period of time. Because the amount of drug delivered to the patient is directly proportional to the amount of current delivered, the drug dosage can be controlled by regulating the amount of current delivered to the patch. As shown in more detail in FIG. 2B, the controller 80 includes the microprocessor 20, which upon execution of software, generates commands to control the various functions of the controller, including but not limited to generating and regulating the current applied to the patch as dictated by a predetermined current delivery profile. To accomplish these functions, the microprocessor 20 is connected to the current generation and regulation circuitry (electronic circuitry), including digital interface and control circuit 30, analog current control circuit 50 and peripheral current control circuitry 40. The peripheral current control circuitry 40 applies the current to the patch 60. The microprocessor 20, digital interface 30, and analog control circuitry 50, together with a memory 10 described in detail below, may comprise an application specific integrated circuit (ASIC). The peripheral current control circuitry 40 is called "peripheral" because it is outside the ASIC. Of course, it will be appreciated that the current generation and regulation circuitry may take on other configurations, and need not be implemented by an ASIC.

The microprocessor 20 is also connected to at least one memory 10 such as random access memory (RAM) or a read-only memory (ROM), in which are stored the current delivery profiles. The controller software may also be stored in the same memory or a separate memory (not shown). The memory 10 may store, for example, each current delivery profile as rate of change of current (di/dt), or current steps, and the time after start-up at which those current steps are to occur. The microprocessor reads the current delivery profile information to generate the appropriately timed commands required to cause the current generation and regulation circuitry to deliver the amount of current dictated by the profile information. In essence, the microprocessor may cycle through the current profile information until the time after start-up matches one of the stored times. At that time, the microprocessor outputs the desired current level, as a digital value, associated with that time to the digital interface of the current circuitry. The digital interface, which includes a digital to analog convertor, converts the digital value to an analog voltage, which will be that voltage required to produce the current level at that point in time of the current delivery profile. The D/A convertor outputs the analog voltage to a voltage-to-current conversion circuit, which generates the required patch current. Feedback from a sensor, such as a current sense resistor, may be used to control the patch current more precisely.

Figure 3A:
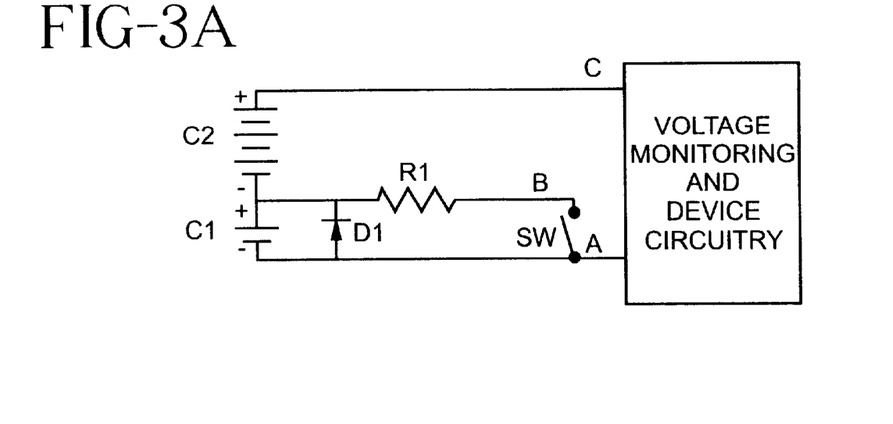
FIGS. 3A–3C depict circuits in accordance with a first embodiment of the present invention.

As stated above, there is a need for a circuit which causes a step in the battery voltage output which can be detected by a voltage monitoring circuit so as to allow the iontophoretic drug delivery system to complete a drug delivery cycle. The first embodiment of the present invention, preferably implemented in the current controller 80, relates to the circuit illustrated in FIG. 3A. In FIG. 3A, C1 and C2 are serially-connected cells that altogether form a battery. C1 and C2 may each comprise one of more individual cells, but for simplicity, will hereinafter be designated as "battery C1" and "battery C2". Each individual cell of battery C1 or battery C2 may be of any compatible electrochemistry type and may be of any voltage. For example, battery C1 may be a single 1.5 Volts silver oxide cell and battery C2 may be three serially-connected 1.5 Volts silver oxide cells, for a total output voltage ($V_{C1}+V_{C2}$), when fully charged, of 6.0 Volts. Moreover, each cell in battery C2 may be individually packaged, or all the cells of battery C2 may be arranged in a single package. All of the cells comprising either battery C1 or C2 are electrically connected anode (positive terminal) to cathode (negative terminal), as in any standard serial connection.

In this circuit, battery C1 is discharged at a higher rate than battery C2, and thus battery C1 will completely discharge before battery C2. This will cause a discernible step in the output voltage across lines A and C, which can be detected by the voltage monitoring circuit shown in FIG. 4A. The detection of the voltage step can be used as an indication that any ongoing task should be the final task attempted by the device, or as a trigger to begin powering down or any other device function. At that time, battery C1 will be bypassed by diode D1 to prevent it from reverse charging, and battery C2 should have sufficient energy to complete any ongoing task or to power-down. Moreover, the voltage step detection can be used to alert the user of the device that the batteries C1 and/or C2 need replacement or recharging, or if the device is disposable that the device should be discarded, after completion of the final task or power-down.

The circuitry for discharging battery C1 at a higher rate than battery C2 comprises diode D1 and resistor R1, as shown in FIG. 3A. One terminal of resistor R1 is connected to the anode of battery C1, and the other terminal of resistor R1 is connected to one terminal of switch SW via line B. The order of the resistor R1 and switch SW may be reversed. The anode of diode D1 is connected to the cathode of battery C1, and the cathode of diode D1 is connected to the anode of battery C1, that is, diode D1 is reverse-biased with respect to battery C1 when battery C1 is charged. The voltage monitoring and device circuitry is connected to the cathode of battery C1 via line A and the anode of battery C2 via line C. Line A is also connected to the other terminal of switch SW. Switch SW may be part of the device circuitry, and is preferably a MOSFET transistor, the gate of which is under microprocessor control (not shown). Closing switch SW connects line B to line A.

Operation and Use

Having described one embodiment of the iontophoretic drug delivery system, including the controller 80 and the patch 60, of the present invention, its operation and use is described below.

Figure 3B:
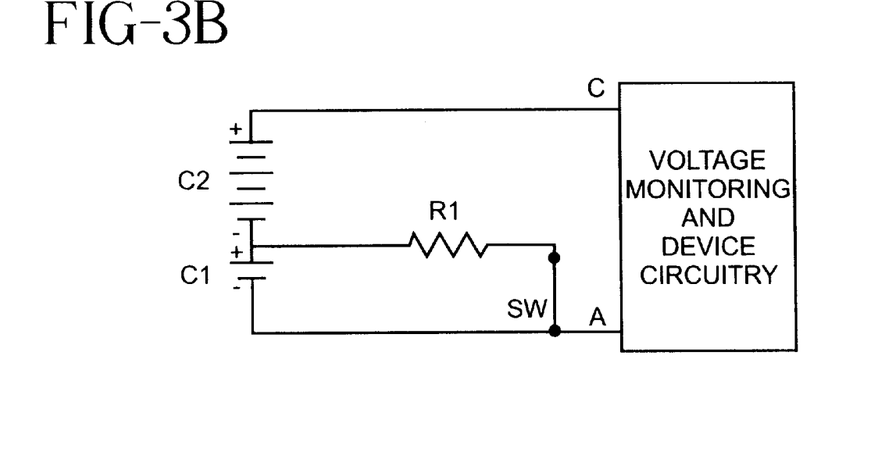
Figure 3C:
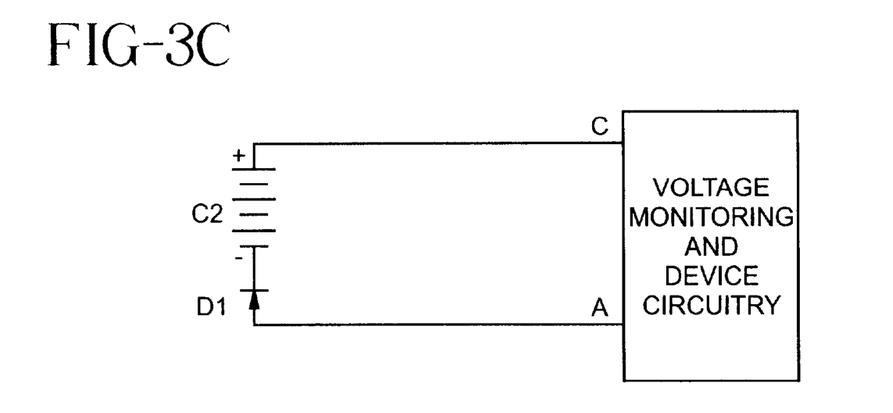

Specifically, the device circuitry of FIG. 3A causes a higher rate of discharge in battery C1 by closing switch SW and connecting line B to line A. Thus, while both batteries C1 and C2 discharge through the device circuitry and voltage monitoring circuitry, battery C1 additionally discharges through resistor R1. Closing of switch SW is preferably performed under computer control by means well known in the art. When battery C1 is fully or substantially charged, diode D1 is reverse-biased with respect to battery C1 and thus acts an open-circuit. The equivalent circuit of this operational state is shown in FIG. 3B. The output voltage across lines C and A is shown in FIG. 5A, and the voltage across lines B and A is shown in FIG. 5B.

Figure 4A:
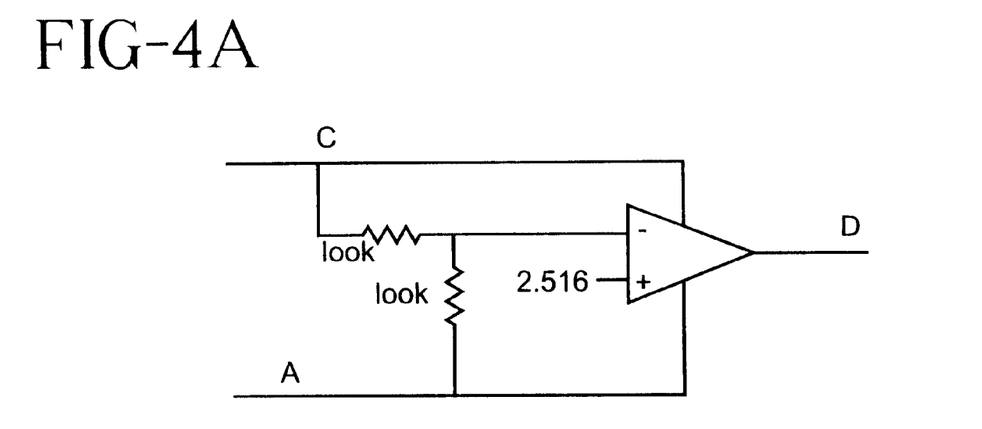
FIG. 4A depicts a voltage monitoring circuit used with the present invention.
Figure 4B:
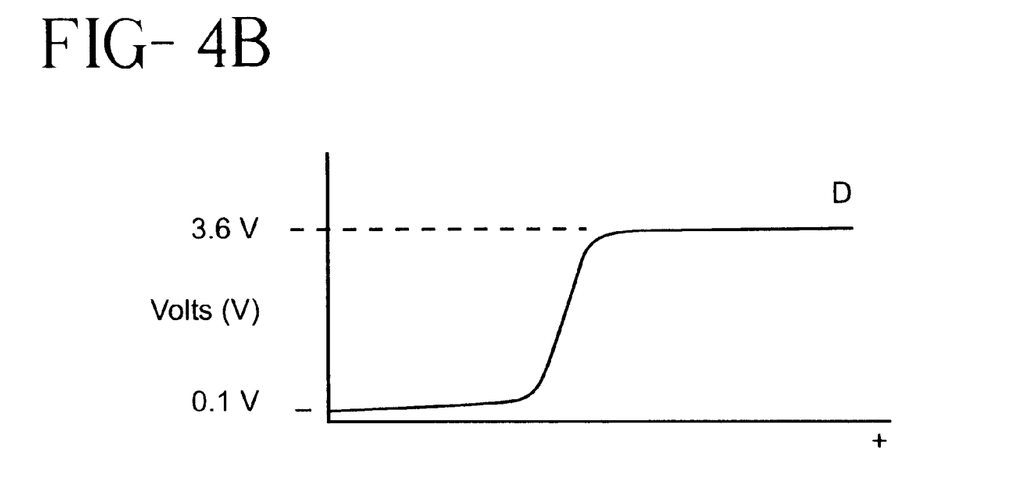
FIG. 4B depicts an illustrative output voltage curve for the voltage monitoring circuit shown in FIG. 4A.
Figure 5A:
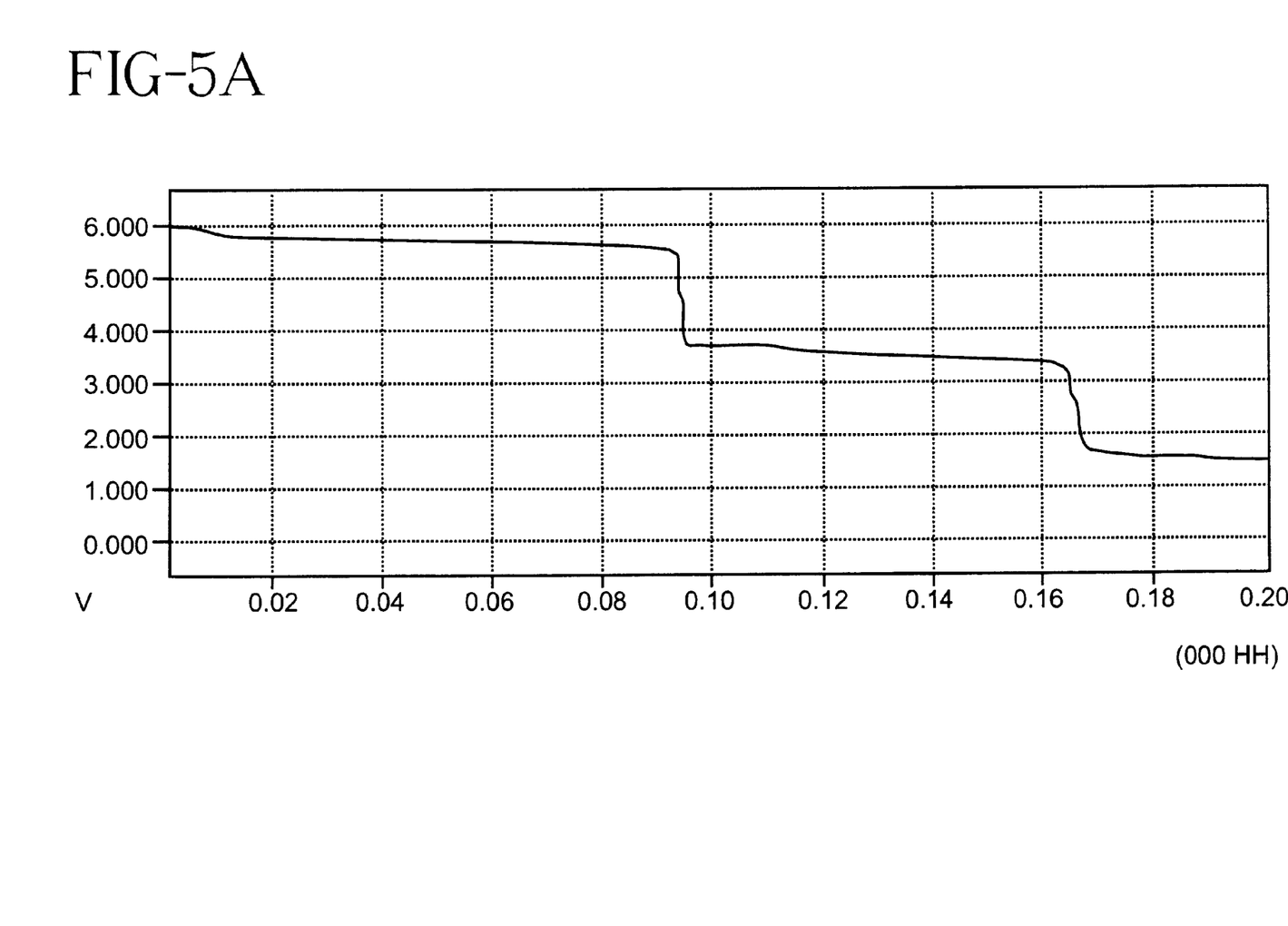
FIGS. 5A and 5B depict output voltage curves in accordance with the first embodiment of the present invention.
Figure 5B:
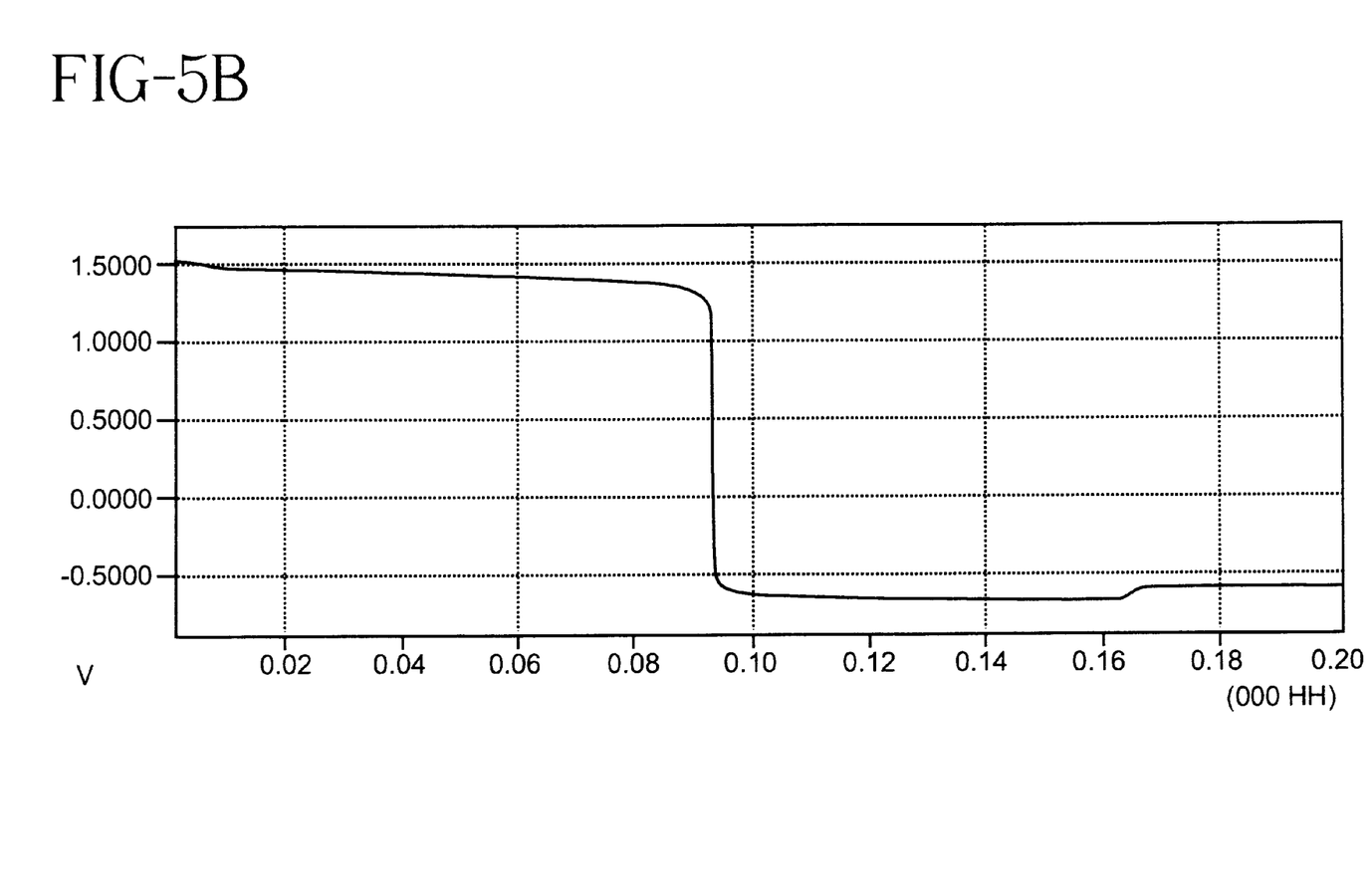

As stated above, both batteries C1 and C2 will eventually discharge over time, but because of the additional discharge of battery C1 through resistor R1, battery C1 will completely discharge before battery C2, as shown in FIG. 5A (battery C1 dies at about 9.4 hours when R1=600 ohms). When battery C1 is completely discharged, it will begin to reverse charge and its voltage becomes a negative value, as shown in FIG. 5B. Diode D1 is now forward-biased with respect to battery C1 and begins to conduct, and the current bypasses battery C1. The device circuitry also disconnects lines A and B via switch SW because there is no longer any need to discharge battery C1, resulting in the equivalent circuit shown in FIG. 3C. The voltage applied to the device circuitry is now $V_{C2}-V_{D1}$ ($V_{D1}$, for example, is about 0.7 Volts). In the example shown in the output voltage curve of FIG. 5A, the output voltage drops from approximately 5.6 Volts to 3.8 Volts when battery C1 dies. This voltage drop causes an easily detectable voltage swing in the output of the voltage monitoring circuitry, shown in FIGS. 4A and 4B and explained in more detail below.

The resistance of resistor R1 will determine the rate of additional discharge of C1, and can be changed to adjust the relative time of discharge between batteries C1 and C2. This time is adjusted so that battery C2 will have sufficient energy after the discharge of C1 for the device to complete any required task or power-down. Alternatively, the controller circuitry, using, for example, the microprocessor 20, can selectively connect and disconnect lines A and B. When lines A and B are disconnected, and line B is open, there is no discharge of battery C1 through resistor R1. Thus, by selectively controlling the connection of line B to line A, the amount of additional discharge, and thus the time of discharge of battery C1, can be additionally adjusted. This selective control may be based on the operating conditions of the device. In summary, (1) by changing the value of resistor R1 or (2) by selectively switching resistor R1 in and out of the circuit (by selectively connecting and disconnecting lines A and B via switch SW), the time when the voltage step occurs can be controlled to vary between 0 and 100% of the life of battery C2.

The device circuitry may include the voltage monitoring circuitry, in which case both the device circuitry and the voltage monitoring circuit would be connected to lines A and C. Alternatively, the voltage monitoring circuitry may be electrically connected to lines A and C but be physically separate from the device circuitry (not shown). In this case, a signaling line must be connected from the voltage monitoring circuitry to the device circuitry so that the voltage monitoring circuitry can send the device circuitry the monitored voltage.

As shown in FIG. 4A, the voltage monitoring circuitry may comprise any standard means for monitoring the output voltage across lines A and C. For example, as shown in FIG. 4A, a simple resistor divider of two 100 kiloohm resistors and a voltage comparator, the positive terminal of which is fixed at 2.5 Volts, comprise the voltage monitoring circuitry. The voltage comparator is powered by lines A and C, and its output is line D, which serves to signal the device circuitry of the occurrence of a voltage drop across lines A and C, as follows. As long as the negative terminal of the voltage comparator remains above the voltage of the positive terminal, in this case 2.5 Volts, output line D will be approximately 0 Volts (ground). When the negative terminal drops below 2.5 Volts, the output line D will shift from 0 Volts to almost the battery voltage (typically, the battery voltage minus a few tenths of a volt). For example, when the voltage across lines A and C is 5.6 Volts, the negative terminal is at half that voltage or 2.8 Volts, and output line D is at approximately 0 Volts. When battery C1 dies and the voltage across lines A and C drops to about 3.8 Volts, the negative terminal is at 1.9 Volts, and the output line rises to approximately 3.6 Volts (the battery voltage of 3.8 Volts minus a few tenths of a volt), as shown in FIG. 4B.

Figure 6:
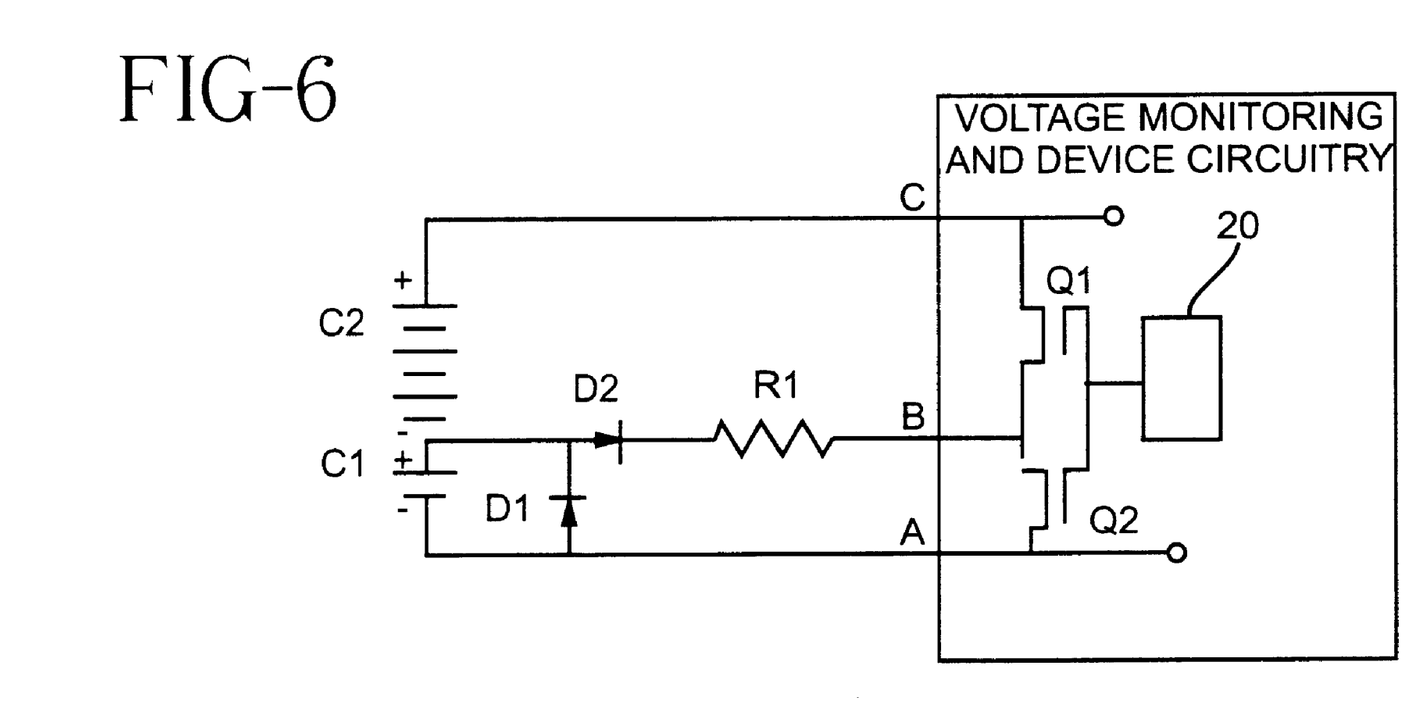
FIG. 6 depicts a circuit in accordance with a second embodiment of the present invention.

A second embodiment of the present invention, which may also be implemented in the iontophoretic current controller 80, is shown in FIG. 6. In this embodiment, lines A and C are connected to a push-pull switch consisting of MOSFETs Q1 and Q2, the gate voltages of which are controlled by a microprocessor (or computer or state machine) 20. In a push-pull switch, when a high voltage is applied to the gates of Q1 and Q2, Q1 is turned off and Q2 is turned on. When a low voltage is applied to the gates, Q2 is turned off and Q1 is turned on. Thus, Q2 acts as a switch between lines A and B, and Q1 acts as a switch between lines B and C. Lines A and C are connected to other device and voltage monitoring circuitry (not shown).

The operation of the circuit of FIG. 6 is similar to that described in the first embodiment, except instead of closing a switch SW, Q2 is turned on by the computer 20 by applying a high voltage to its gate, thus connecting the lines A and B and causing battery C1 to discharge through resistor R1. The diode D2 is forward-biased and will allow current to pass through R1 (R1 and D2 may be interchangeably connected). Transistor Q1 is turned off and line B is disconnected from line C. When transistor Q2 is turned off by applying a low voltage to its base, either to control selectively the rate of discharge of battery C1 or because battery C1 has already discharged, Q1 is turned on, connecting lines B and C. In this case, diode D2 is reverse-biased and turned off, and no current may flow through resistor R1. When battery C1 is discharged, D1 turns on, allowing the current to bypass battery C1 as previously described.

In addition, the circuits of the first and second embodiments can be duplicated to provide multiple voltage steps during the discharge of the batteries. For example, the circuit shown in FIG. 7 discharges two batteries at different, higher rates so as to result in two voltage output steps. In this circuit, battery C3 is additionally discharged through resistor R2 after battery C1 has been completely discharged and bypassed by diode D1. This is accomplished by disconnecting line B from line A, and connecting line E to line A, after the voltage monitoring circuitry has detected the first voltage step.

Figure 7:
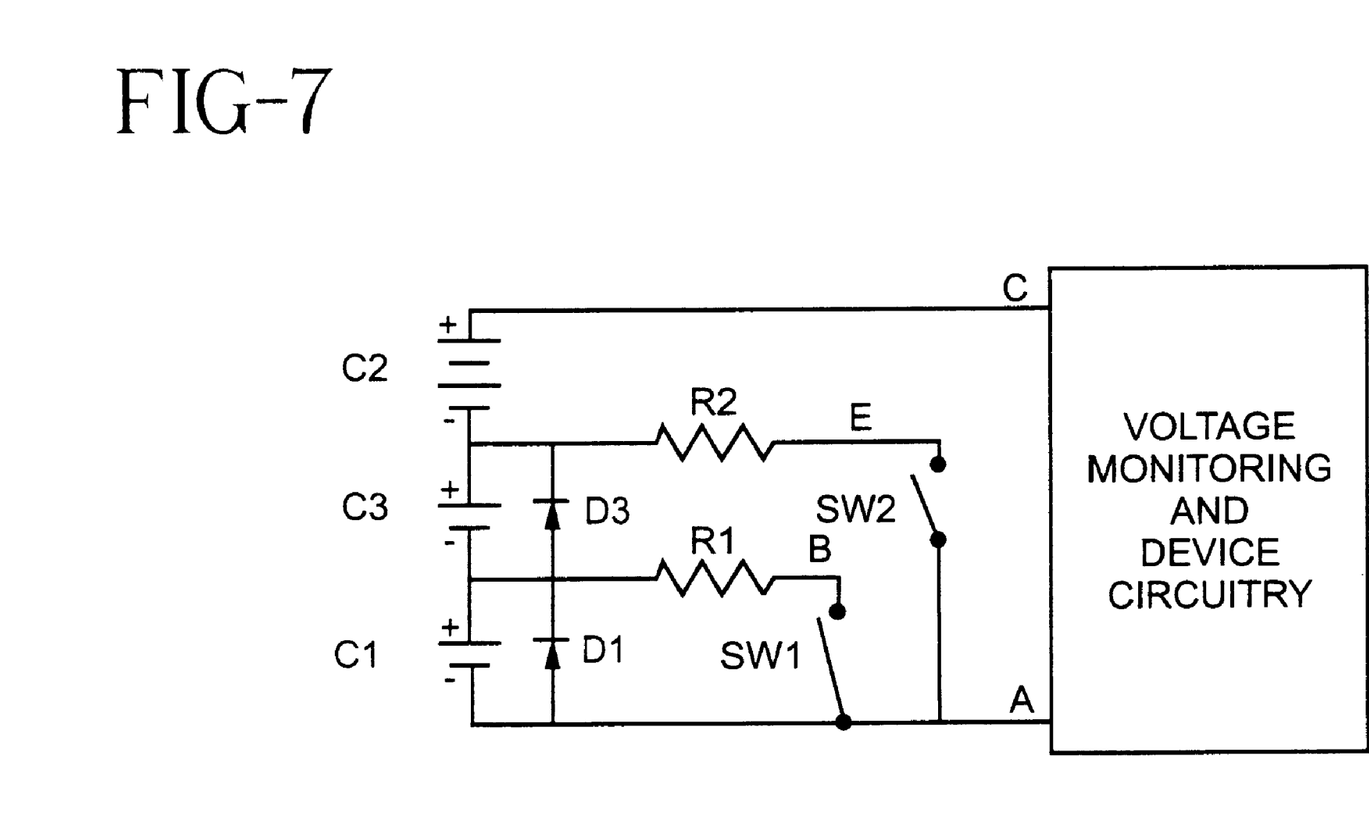
FIG. 7 depicts a circuit in accordance with a third embodiment of the present invention.

In particular, diodes D1 and D3 are reversed-biased to batteries C1 and C3 respectively, and thus act as open-circuits when batteries C1 and C3 are fully or substantially charged. Line B is connected to line A by closing switch SW1 (which may be interchangeably connected with R1) and line E is disconnected from line A by opening switch SW2 (which may be interchangeably connected with R2). Thus, battery C1 is discharged through resistor R1, as in the first embodiment. The output voltage is $V_{C1}+V_{C2}+V_{C3}$. When battery C1 discharges and begins to reverse charge, diode D1 turns on and conducts, causing the current to bypass battery C1. Upon detection of the first voltage step by the voltage monitoring circuitry, the device circuitry disconnects line B from line A by opening switch SW1 and connects line E to line A by closing switch SW2. Diode D3 is still reverse-biased, so battery C3 discharges through resistor R2. The output voltage is $V_{C2}+V_{C3}-V_{D1}$. The output voltage is monitored to detect the second voltage step when battery C3 discharges. Battery C3 will discharge before battery C2 because of the additional discharge through resistor R2. When battery C3 is completely discharged and begins to reverse charge, diode D3 turns on and conducts, causing the current to bypass battery C3. Upon detection of the second voltage step, the device circuitry disconnects line E from line A. The output voltage is now $V_{C2}-V_{D1}-V_{D3}$ ($V_{D3}$ is about 0.7 Volts). Thus, two steps in the output voltage can be accomplished by duplicating the circuitry as shown in the third embodiment. More than two voltage steps can be achieved by further duplicating the cell discharge/bypass circuitry.

Active agent, drug, formulation, medication, medicament and active compound have been used herein to mean any ethical pharmaceutical compound or agent, such as therapeutic compounds, diagnostic agents, anesthetic agents and the like.

As is well known within the field, the device can be situated on the area of the patient to which the active agent is to be applied (the applied area) such as the skin and a voltage impressed across the anode 61 and cathode 62 to cause electrical current to flow through the skin of the patient to drive or otherwise transport the drug preferably in the form of an ionic active agent into the skin and the tissue to be absorbed by the body of the patient. The electric field lines are sufficiently long, however, so that the active agent is transported to the desired depth within the skin, and possibly to the vasculature, to provide the desired effect, e.g., anesthetic, therapeutic or diagnostic. It should also be appreciated that the device of the present invention can be applied to other areas of the body such as mucus membranes depending upon the desired therapy and drugs to be delivered.

In addition, while the present invention has been described in connection with iontophoresis, it should be appreciated that it may be used in connection with other principles of active introduction, i.e., motive forces, such as electrophoresis which includes the movement of particles in an electric field toward one or other electric pole, anode, or cathode and electro-osmosis which includes the transport of uncharged compounds due to the bulk flow of water induced by an electric field. Also, it should be appreciated that the patient may include humans as well as animals.

Of course, it will be appreciated that the invention may also take forms other than those specifically described, and is not limited to its implementation in controllers of iontophoretic drug delivery systems. For example, the above-described circuits may be implemented in any electrical or electronic device, especially that which requires one or more voltage steps and/or the precise control thereof, and in which employment of a conventional voltage-stepped battery is impractical or insufficient. The scope of the invention, however, is to be determined solely by the following claims.

What is claimed is:

1. A controller for use in combination with a patch to form an operable iontophoretic drug delivery system, said controller comprising:

electronic circuitry including a circuit for causing a higher rate of discharge of at least one of a plurality of serially-connected cells forming a battery, the battery capable of supplying a current to a device, said circuit having a switch connected to a first electrode of the at least one cell;

a resistor connected in series with said switch and to a second electrode of the at least one cell, the at least one cell additionally discharging through said resistor when said switch is closed; and a reversed bias diode connected between said first electrode and said second electrode of the at least one cell so that said diode is in parallel with said resistor when said switch is closed, and in parallel to the at least one cell, said reversed-biased diode causing the current to bypass the at least one cell when the at least one cell has died.

2. A controller according to claim 1, wherein the closing of said switch is controlled by the device.

3. A controller according to claim 1, wherein said switch is an electronic switch.

4. A controller according to claim 1, wherein the battery is also connected to a voltage monitoring circuit.

5. A controller according to claim 4, wherein the voltage monitoring circuit detects a voltage step when the at least one cell has died and sends a voltage step detection signal to the device.

* * * * *